(12) United States Patent
Keppler

(10) Patent No.: US 10,010,334 B2
(45) Date of Patent: Jul. 3, 2018

(54) CONTOUR LOCK GUIDES

(71) Applicant: MATERIALISE N.V., Leuven (BE)

(72) Inventor: Louis Keppler, Valley City, OH (US)

(73) Assignee: Materialise, Leuven (BE)

( * ) Notice: Subject to any disclaimer, the term of this patent is extended or adjusted under 35 U.S.C. 154(b) by 0 days.

(21) Appl. No.: 15/239,960

(22) Filed: Aug. 18, 2016

(65) Prior Publication Data

US 2018/0070964 A1  Mar. 15, 2018

Related U.S. Application Data

(63) Continuation of application No. 14/221,784, filed on Mar. 21, 2014, now Pat. No. 9,421,021, which is a continuation of application No. PCT/EP2012/068540, filed on Sep. 20, 2012.

(60) Provisional application No. 61/537,165, filed on Sep. 21, 2011.

(51) Int. Cl.
*A61B 17/17* (2006.01)
*A61B 17/56* (2006.01)

(52) U.S. Cl.
CPC ...... *A61B 17/1739* (2013.01); *A61B 17/1746* (2013.01); *A61B 17/1778* (2016.11); *A61B 2017/568* (2013.01)

(58) Field of Classification Search
CPC ............ A61B 17/1739; A61B 17/1746; A61B 17/1778; A61B 2017/568
See application file for complete search history.

(56) References Cited

U.S. PATENT DOCUMENTS

| 2006/0079963 A1* | 4/2006 | Hansen | A61F 2/40 623/19.11 |
| 2010/0023015 A1* | 1/2010 | Park | A61B 17/15 606/87 |
| 2011/0190775 A1 | 8/2011 | Ure | |

FOREIGN PATENT DOCUMENTS

| WO | 2011060536 A1 | 5/2011 |
| WO | 2012021241 A2 | 2/2012 |
| WO | 2012058349 A2 | 5/2012 |

OTHER PUBLICATIONS

International Preliminary Report on Patentability dated Apr. 3, 2014 for related application PCT/EP2012/068540 filed Sep. 20, 2012 (copy submitted in parent application).
International Search Report dated Jan. 8, 2013 for related application PCT/EP2012/068540 filed Sep. 20, 2012 (copy submitted in parent application).

\* cited by examiner

*Primary Examiner* — Christian Sevilla
(74) *Attorney, Agent, or Firm* — Patterson & Sheridan LLP

(57) ABSTRACT

Provided herein are patient-specific surgical guiding tools for positioning on a socket of a ball-and-socket joint, e.g., an acetabulum. The guiding tools comprise a central contact element fitting within the socket and one or more lateral contact elements fitting on the rim of the socket. The guiding tools allow accurate positioning of surgical tools such as alignment elements, according to a pre-operational planning. Methods for the manufacture and use of said guiding tools are also provided.

10 Claims, 5 Drawing Sheets

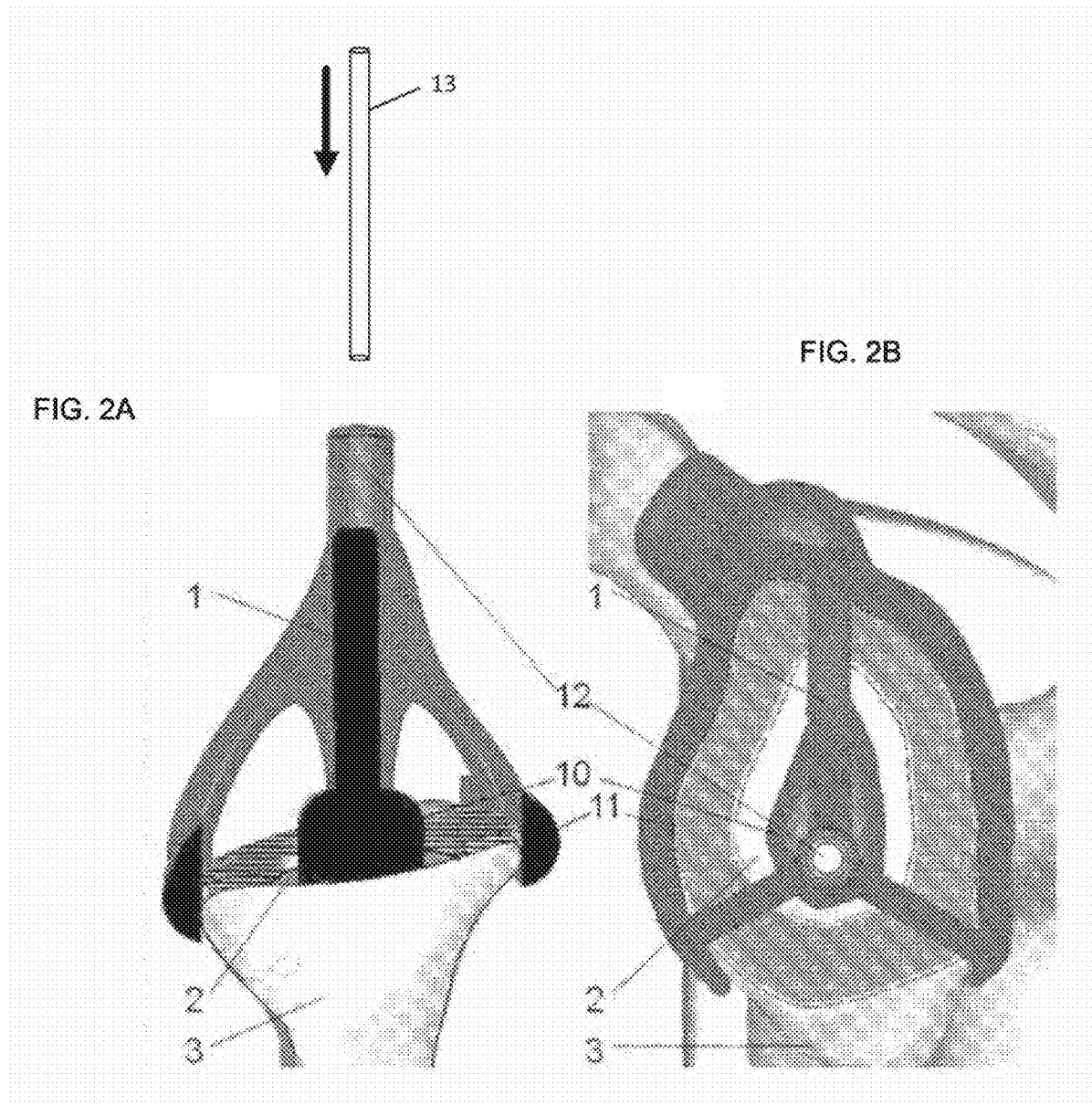

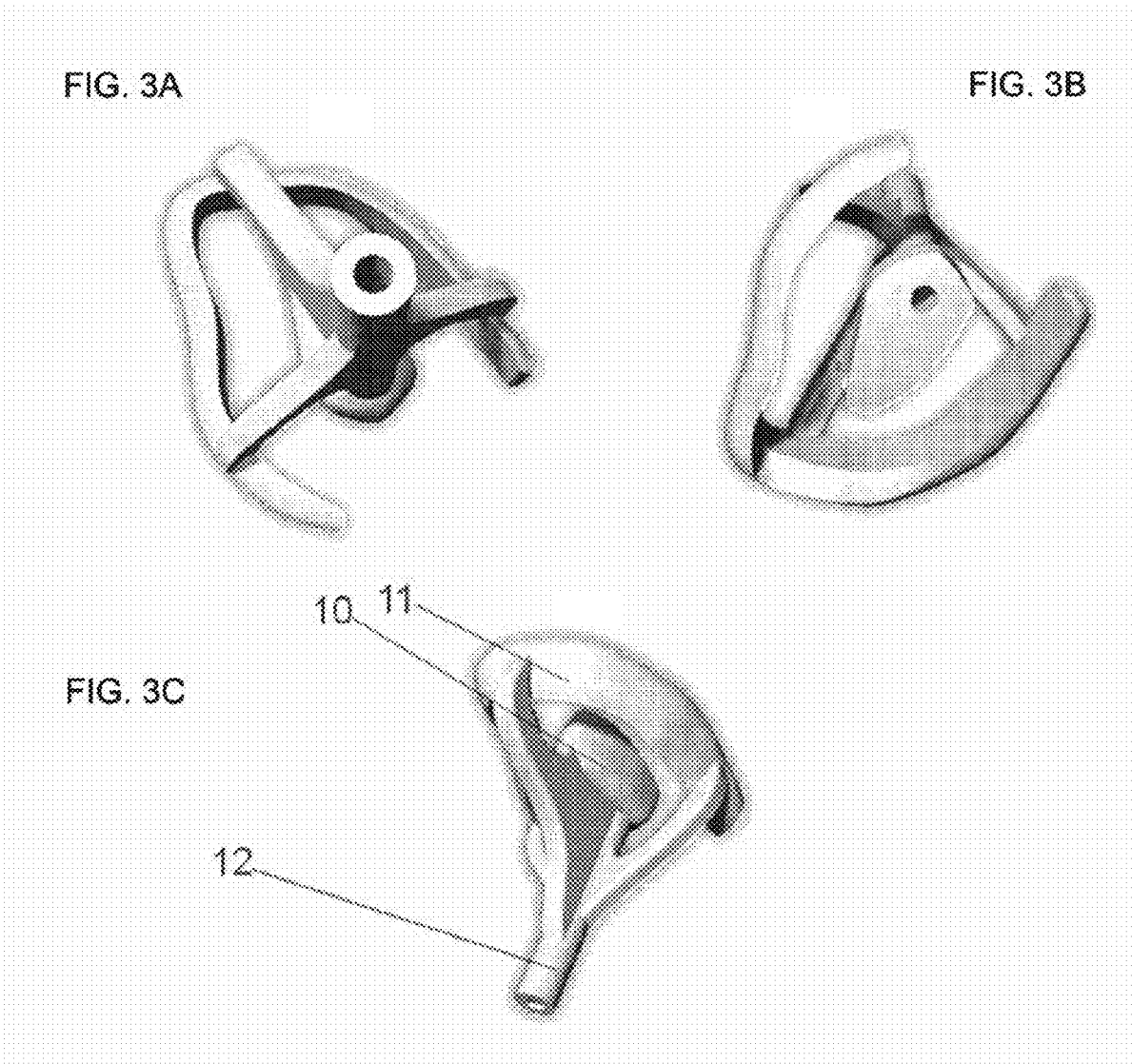

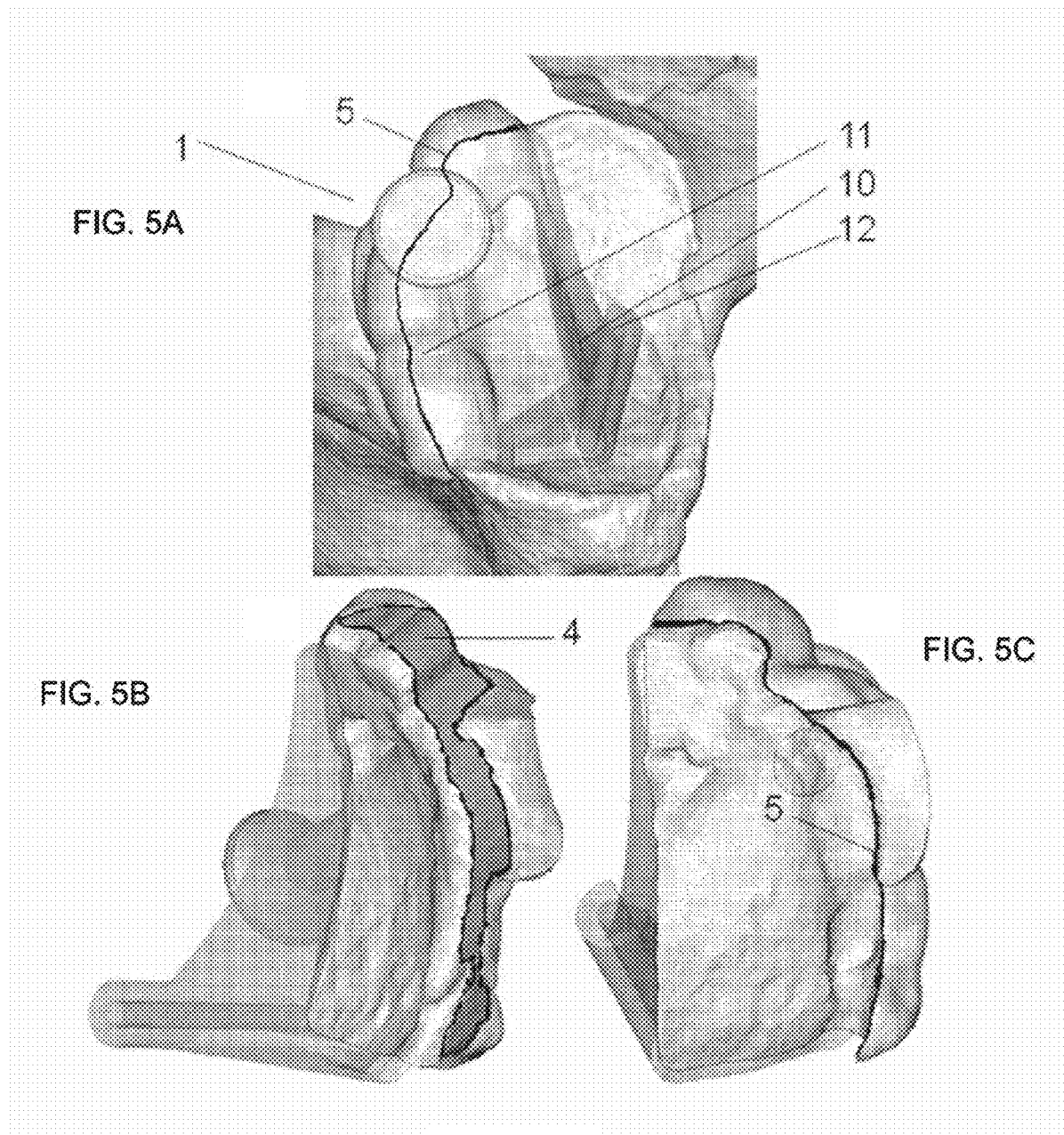

CONTOUR LOCK GUIDES

CROSS-REFERENCE TO RELATED APPLICATIONS

This application is a continuation of U.S. application Ser. No. 14/221,784, filed Mar. 21, 2014 (and issued as U.S. Pat. No. 9,421,021 on Aug. 23, 2016), which is a continuation under 35 U.S.C. § 120 of International Application No. PCT/EP2012/068540, filed Sep. 20, 2012 (and published by the International Bureau as WO 2013/041622 on Mar. 28, 2013), which claims the benefit of U.S. Provisional Patent No. 61/537,165, filed Sep. 21, 2011. Each of the above-referenced patent applications is hereby incorporated by reference in its entirety.

BACKGROUND OF THE INVENTION

Field of the Invention

Provided herein are patient-specific surgical guiding tools for positioning on a socket of a ball-and-socket joint, e.g. a glenoid cavity. The guiding tools allow accurate positioning of surgical tools such as alignment elements, according to pre-operational planning. Methods for the manufacture and use of the guiding tools are also provided.

Description of the Related Technology

In most joint arthroplasty, replacement and/or reconstruction surgery procedures, the joint is replaced by a prosthetic implant. The main goal of such interventions is to relieve (arthritic) pain and/or to restore severe physical joint damage. When a prosthesis fails, a revision surgery is carried out. However, this procedure is technically more difficult and time-consuming than the primary intervention and the outcome is often less satisfactory. Furthermore, with each successive joint revision, the risk of infection and symptomatic loosening of the prosthesis may increase substantially. Accordingly, one of the most important aspects of joint surgery procedures is the correct, accurate and stable placement of the primary implant.

In order to improve the accuracy of surgical procedures in general, various custom made, patient-specific orthopedic guides are available. These custom guides may be used to accurately place pins, guide bone cuts, and insert implants during orthopedic procedures.

Typically, the guides are made from a pre-operative plan formed from an MRI or CT scan of the patient and rely on the matching of a subcutaneous anatomic feature for correct positioning of the guide according to pre-operational planning. Typically, these guides rely on a direct surface contact with the defined anatomy. The contact surface is generally bone and/or cartilage, although guides contacting other soft tissues than cartilage have been developed.

However, certain anatomies cannot be contacted with a surface matched guide because the exact tissue shape cannot be determined, the tissue is too soft to provide a stable position for the guide, and/or the tissues are too vulnerable to be contacted with the guide. For example, surgical guides for use in shoulder joint surgery cannot fit accurately onto the glenoid labrum which surrounds the glenoid fossa. This makes it difficult to design compact and accurate surgical guides for shoulder joint surgery, especially because the surface of the glenoid fossa itself is not adequate to achieve a unique fit position.

Accordingly, there is a need for improved surgical guiding tools for joint surgery.

SUMMARY

The present application relates to surgical guiding tools for positioning on the socket of a ball-and-socket joint which do not require any contact with the socket labrum or ligaments. The current application provides a device and method for creating a locking position over such anatomies by using the contour of the anatomy and avoiding the untouchable surface. This contour thus provides a rotational lock by creating a surface which contacts the contour of the anatomy, but does not require a surface fit in this region.

In a first aspect, provided herein is a patient-specific surgical guiding tool for positioning an alignment element on the socket of a ball-and-socket joint, or into the bone surrounding the socket, comprising a central contact element which fits onto an area within the socket of the ball-and-socket joint and one or more lateral contact elements which fit onto the rim of the socket and/or the bone surrounding the socket and/or the ligament around the socket. The guiding tool may further include a positioning element provided with an opening which allows the insertion of the alignment element. In some particular embodiments, the elements are provided as one integrated structure for simultaneous positioning on the bone. Optionally, the central and lateral contact elements are provided as one integrated structure and the positioning element is removably attached thereto.

In particular embodiments, the guiding tool as described herein comprises one lateral contact element corresponding to at least part of the outer contour of the socket and the central contact element corresponds to at least part of the inner contour of the socket. In particular embodiments, the one or more lateral contact elements are designed to contact the rim of the socket of the ball and socket joint in at least three contact points, wherein the angle between a first line connecting one contact point and the center of the circle or ellipse best fitting the rim of the socket and a second line connecting the adjacent contact point and the center is never greater than 180 degrees.

In some embodiments, the guiding tool comprises at least two lateral contact elements which fit onto areas around the socket in at least three contact points, wherein the angle between a first line connecting one contact point at the center of the circle or ellipse best fitting the rim of the socket and a second line connecting the adjacent contact point and the center is never greater than 180°.

In certain embodiments, the at least three contact points are repetitively provided onto the one or more lateral contact elements, over a distance of at least 5 mm. In further embodiments, the at least three contact points are repetitively provided over a distance of at least 5 mm along the direction of the longitudinal axis of the opening of the positioning element. In further embodiments, the at least three contact points are repetitively provided over a distance of at least 5 mm, 7 mm, 10 mm or 15 mm along the direction of the longitudinal axis of the opening of the positioning element.

In particular embodiments, the guiding tool as described herein further comprises a connecting structure, wherein the lateral connecting elements extend from the connecting structure. In further embodiments, the connecting structure corresponds with the positioning element.

In certain embodiments, at least one of the one or more lateral contact elements is further positioned on the guiding tool such that, when positioned on the bone, it interacts with an anatomical feature around the socket. In particular embodiments, the alignment element is selected from the group comprising a pin, a wire, a screw and a drill. Moreover, the positioning element corresponds to one of the central or lateral contact elements. In certain embodiments, the guiding tool as described herein is manufactured via additive manufacturing.

In still other embodiments, a further aspect provides a method for the manufacture of a guiding tool comprising obtaining volume information of the socket of a ball-and-socket joint from a patient and obtaining the installation direction of a socket implant for the patient. The method further may include identifying and selecting parts of the bone surrounding the socket which are suitable for lateral contact elements and designing and producing a surgical guiding tool based on the obtained volume information and installation direction.

In yet another embodiment, a methods for positioning an alignment element into the bone of a socket or into the bone surrounding the socket are provided. The method may include positioning a surgical guiding tool onto the socket and using the hole provided by the positioning element of the guiding tool to insert the alignment element into the bone of or around the socket. The guiding tool may then be removed from the socket. In some embodiments, the removal of the guiding tool from the socket may include removing the guiding tool along the direction of the longitudinal axis of the alignment element.

The patient may be an animal or human patient. Therefore the socket may be any socket of a ball-and-socket joint in an animal or human body. In human patients, the socket of a ball-and-socket joint may be a glenoid cavity or an acetabulum. In particular embodiments, the socket is a glenoid cavity.

The design of the patient specific surgical guiding tools as described herein ensures that the guiding tools, and therefore also the alignment element, can be accurately positioned onto a socket of a ball-and-socket joint without contacting the ligaments surrounding the socket. The contact with the contour of the socket structure provides a rotational lock of the guide, whereas the fit on the socket cavity ensures the correct depth position of the guide.

BRIEF DESCRIPTION OF THE DRAWINGS

The following description of the figures of specific embodiments is merely exemplary in nature and is not intended to limit the present teachings, their application or uses. Throughout the drawings, corresponding reference numerals indicate like or corresponding parts and features.

FIG. 2A is a side view of a surgical guiding tool (1) according to a particular embodiment, positioned on a glenoid cavity (2) of the ball-and-socket joint (3).

FIG. 2B is a top view of a surgical guiding tool (1) according to a particular embodiment, positioned on a glenoid cavity (2) of a ball-and-socket joint (3).

FIG. 3A is a perspective view of a surgical guiding tool (1) according to a particular embodiment.

FIG. 3B is a perspective view of a surgical guiding tool (1) according to a particular embodiment.

FIG. 3C is a perspective view of a surgical guiding tool (1) according to a particular embodiment.

FIGS. 5A-5C are illustrations of the position of the surgical guiding tool (1) onto the glenoid and the contact it makes with the outer surface of the glenoid socket.

Figure 1A:
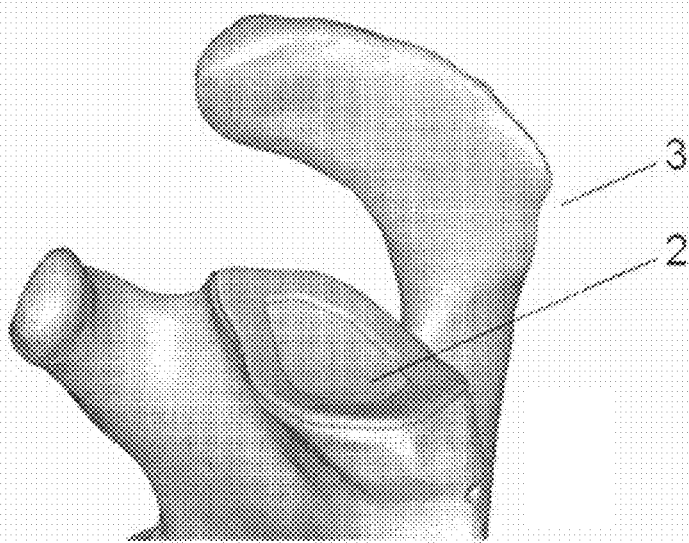
FIG. 1A is a perspective view of a ball-and-socket joint (3) and the glenoid cavity (2) of a ball-and-socket joint (3).

In the figures, the following numbering is used 1—ball-and-socket joint; 2—glenoid cavity; 3—surgical guiding tool; 4—contour surface; 5—contour line.

DETAILED DESCRIPTION OF CERTAIN INVENTIVE EMBODIMENTS

The present invention will be described with respect to particular embodiments but the invention is not limited thereto but only by the claims. Any reference signs in the claims shall not be construed as limiting the scope thereof.

As used herein, the singular forms "a", "an", and "the" include both singular and plural referents unless the context clearly dictates otherwise.

The terms "comprising", "comprises" and "comprised of as used herein are synonymous with "including", "includes" or "containing", "contains", and are inclusive or open-ended and do not exclude additional, non-recited members, elements or method steps. The terms "comprising", "comprises" and "comprised of when referring to recited members, elements or method steps also include embodiments which "consist of the recited members, elements or method steps.

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments described herein are capable of operation in other sequences than described or illustrated herein.

The term "about" as used herein when referring to a measurable value such as a parameter, an amount, a temporal duration, and the like, is meant to encompass variations of +/−10% or less, preferably +1-5% or less, more preferably +/−1% or less, and still more preferably +/−0.1% or less of and from the specified value, insofar such variations are appropriate to perform. It is to be understood that the value to which the modifier "about" refers is itself also specifically, and preferably, disclosed.

The recitation of numerical ranges by endpoints includes all numbers and fractions subsumed within the respective ranges, as well as the recited endpoints.

All documents cited in the present specification are hereby incorporated by reference in their entirety.

Unless otherwise defined, all terms used herein, including technical and scientific terms, have the meaning as commonly understood by one of ordinary skill in the art. By means of further guidance, definitions for the terms used in the description are included to better appreciate the teaching herein. The terms or definitions used herein are provided solely to aid in the understanding of the application.

The present application provides in a patient-specific surgical guiding tool for positioning an alignment element and/or for guiding a surgical instrument. The alignment element may be used for indicating a (pre-operationally planned) direction and/or position for an implant. The guiding tool comprises patient specific contact elements, which fit onto areas on and/or around a socket; the guiding tool further comprises at least one positioning element for positioning the alignment element.

The devices envisaged herein are of particular interest to the field of implant surgery, more particularly in the context of implants which are placed into a socket of a ball-and-socket joint. For human patients, this is a glenoid implant and/or an acetabular cup implant. The term "glenoid implant" as used herein refers to a component of a prosthetic shoulder implant which is placed into or onto the glenoid cavity of a patient. Such implants may be used in a (total) shoulder arthroplasty or reverse (total) shoulder arthroplasty. The glenoid cavity, also known as glenoid fossa (of the scapula), is a shallow surface, which is located on the lateral angle of the scapula. This cavity forms the glenohumeral joint along with the humerus. The term "acetabular cup implant" as used herein refers to the component of a prosthetic hip implant which is placed into the acetabulum of a patient. The acetabulum is a concave surface of the pelvis, where the head of the femur meets with the pelvis, thus forming the hip joint. The term "contour, as used herein refers to the outline of an anatomical feature, typically represented by the edge or line that defines or bounds the shape of the anatomical feature. For a socket anatomy the contour line may coincide with the rim or edge of the socket. Contour surfaces include surfaces extending from the contour line towards the inside of the socket, also referred to as inner contour surface, while outer contour surfaces are referred to as surfaces extending from the contour line outwards and typically comprise anatomical areas outside the socket.

The terms "rim" and "socket rim" as used herein refer to the edge of a socket. Usually, this is a substantially convex edge of the concave bone surface which forms the socket. For human patients, particular examples are the glenoid rim and/or the acetabular rim. The term "glenoid rim" as used herein refers to the edge of the glenoid cavity, more particularly the substantially convex edge of the concave surface of the scapula which forms the glenoid cavity. The term "acetabular rim" as used herein refers to the edge of the acetabulum, more particularly the substantially convex edge of the concave surface of the pelvis which forms the acetabulum.

The term "socket" as used herein in the context of a ball joint, refers to a socket of a ball- and-socket joint of the human or animal body. For human patients, typical examples include the glenoid cavity and/or the acetabulum.

The term "alignment element" as used herein refers to an element which facilitates the correct positioning of an implant into or onto an anatomical socket, for example by indicating a certain location and/or direction for positioning and/or by physically guiding the implant or an implant guide to a certain location. Without such element, the implant may be positioned incorrectly, leading to suboptimal functioning of the prosthesis and discomfort to the patient.

The terms "surgical guiding tool" and "guiding tool" as used herein refer to (patient-specific) surgical tools that can be positioned onto an anatomical part of a patient and that help a surgeon in the positioning of an alignment element and/or other surgical instruments. Reference throughout this specification to "one embodiment" or "an embodiment" means that a particular feature, structure or characteristic described in connection with the embodiment is included in at least one embodiment. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

The present application provides surgical guiding tools for facilitating the positioning of an implant into or onto a socket of a ball-and-socket joint in the body of an animal or human patient. More particularly, in the context of humans, provided herein are surgical guiding tools for positioning an alignment element, which can be used for positioning a glenoid implant or an acetabular cup implant. However the surgical guiding tools described herein are equally useful for use in animals.

The surgical guiding tools as described herein comprise at least one central contact element and one lateral contact element. Together, the central and lateral contact elements ensure the correct positioning of the surgical guiding tool by contacting specific locations on the patient's anatomy. In the surgical guiding tools envisaged herein, the central and lateral contact elements are typically integrated in a one-piece structure which is made to specifically fit an individual patient's anatomy.

The central contact element of the guiding tool as described herein is provided with a patient-specific surface which fits onto an area within a patient's socket, hereinafter also referred to as "socket contact area". The socket contact area typically spans an area which varies between one square micrometer ($\mu m^2$) and fifty square centimeters ($cm^2$). In particular embodiments, the socket contact area corresponds to at least 10, 20, 30, 40, 50, 60, 70, 80 or 90 percent of the total socket area. In certain embodiments, the socket contact area corresponds to the total area of the socket. The central contact element may provide an indication of the planned position of the guiding tool on the socket. However, the concave surface of the socket alone typically is not sufficient to provide a stable and/or unique fit position. In order to ensure a stable and unique fit position, the guiding tool as described herein further comprises one or more lateral contact elements connected thereto, which fit onto specific areas around the socket.

Thus, the central and lateral contact elements ensure the correct positioning of the guiding tool according to pre-operational planning.

However, the socket is typically surrounded by a (fibro) cartilaginous rim, which does not provide reliable or useful areas for contacting. This cartilaginous rim is typically referred to as socket "labrum" or "ligament(s)", e.g. the glenoid labrum or the acetabular labrum. Where the socket labrum does not provide any useful areas for contacting, the lateral contact element(s) fit onto the anatomy surrounding both the socket and the socket labrum.

In order to ensure stability of the guiding tool when positioned on the socket, the lateral contact elements typically are designed to contact the outer contour of the acetabular rim. In particular embodiments the lateral contact elements contact the acetabulum exclusively on the exterior of the acetabulum. In some embodiments, the contact elements can extend over the acetabular labrum and a section of the exterior of the acetabulum. In further particular embodiments one or more of the one or more contact elements can extend (transversally to the socket) from the interior surface of the socket towards the exterior surface of the bone comprising the socket.

The one or more lateral contact elements can be designed to make contact with the acetabulum in either discrete contact points spread over the rim of the socket which are interconnected or in a continuous element extending over a section of the rim of the socket. In particular embodiments, the one or more contact elements extend (longitudinally following the rim of the socket) over a section of the socket rim or labrum, more particularly over an section corresponding to 30° or more, 45° or more, more particularly 60° or more and more particularly 90° to 120° of the contour of the socket.

In further particular embodiments, one contact element is provided which contacts the acetabulum over an angular area of between 45° and 120° of the contour of the socket. In particular embodiments, the lateral contact elements fit onto specific areas of the rim of the socket in at least three discrete (i.e. non-continuous) contact points which are spaced apart on the rim of the socket. In particular embodiments, the contact elements are distributed over at least a section of the rim so as to ensure that when the guiding tool is positioned onto the socket, a rotational stability is obtained.

In a particular embodiment, the contact points have an arrangement so as to surround the socket and the socket labrum, whereby the angle between the line connecting one contact point and the center of the circle or ellipse best fitting the socket rim, and the line connecting the adjacent contact point and the center of the circle or ellipse best fitting the socket rim is never greater than 180°.

In particular embodiments, the angle between the contact points (as determined by lines connecting each contact point with the center of the circle of ellipse) is never greater than 175, 170, 165, 160, 155, 150, 145, 140, 135, 130, 125, 120, 115, 110, 105, 100, 95 or 90°. This will be explained in further detail herein below.

In particular embodiments, guiding tools are provided wherein the contact points have a circular or substantially circular arrangement, preferably so as to surround the acetabulum, wherein the angle defined by two adjacent contact points is never greater than 180°. In other words, the angle between the line connecting one contact point and the center of the circle best fitting the acetabular rim and the line connecting the adjacent contact point and the center is never greater than 180°. Hereby the acetabulum is considered to have a substantially circular shape.

The glenoid cavity on the other hand, can be considered piriform. Thus, the glenoid cavity comprises a substantially circular shape on one side, but tapering towards the other side. Therefore, to ensure positional stability of the guiding tool onto a glenoid cavity, guiding tools may be provided wherein the contact points have a circular or substantially circular arrangement around the circumference of the rim of the glenoid cavity. More particularly, the angle formed by a first line drawn between one contact point and the center of the circle best fitting the (substantially circular part of) the glenoid cavity rim and a second line drawn between the adjacent contact point and the center is never greater than 180°. This can also be expressed in terms of the sector angle defined by two adjacent contact points which is never greater than 180°. Alternatively, the glenoid cavity may be considered as having a roughly elliptical shape. In that case, to ensure positional stability of the guiding tool onto a glenoid cavity, the contact points have an arrangement, wherein the angle 0 between the (straight) line connecting one contact point and the center of the ellipse best fitting the glenoid cavity rim and the (straight) line connecting an adjacent contact point and the center is never greater than 180°. Again this can be expressed by the fact that the sector angle defined by two adjacent contact points is never greater than 180°.

Thus, more generally for an undefined socket, in particular embodiments of the guiding tools as described herein, the lateral contact elements fit onto areas surrounding the socket and socket labrum in at least three contact points, wherein the contact points have an arrangement so as to surround the socket, wherein the angle between a line drawn between one contact point and the center of the circle or ellipse best fitting the socket rim and a second line drawn between an adjacent contact point and the center is never greater than 180°; or similarly, the sector angle defined by two adjacent contact points is never greater than 180°. These contact points may all be located on the same lateral contact element (i.e. one contact element comprises these three contact points), or distributed over two or more lateral contact elements.

In particular embodiments, as described herein above, rotational stability of the guiding tool onto a socket in general or an acetabulum or glenoid cavity in particular, may be provided through the provision of one or more contact elements with contact points which extend over the rim of the socket (from the inside rim of the socket towards the exterior surface of the bone).

In particular embodiments, the surgical tools as described comprise one or more contact elements which extend over an angular distance of at least 30° of the contour of the socket.

In certain embodiments, the one or more lateral contact elements of the surgical guiding tools as described herein contain, on the surface which is intended for placement on the bone, patient-specific surfaces, i.e. anatomy engagement surfaces which at least partially match the surface around the socket and socket labrum. This implies that the contact element comprises of a plurality of contact points (corresponding to a contact surface). In particular embodiments, the surgical guiding tools as described herein comprise only one lateral contact element, which has a single contact surface extending longitudinally over a section of the rim of the socket. In particular embodiments, the contact surface spans the surface on the exterior of the socket and optionally over the socket labrum over an angle of at least 30°. In further particular embodiments, the contact element extends longitudinally along the rim of the socket over a stretch corresponding to between 30° and 180°. Alternatively, the surgical guiding tools as described herein may comprise more than one lateral contact element, each comprising one or more patient-specific contact surfaces. In particular embodiments, rotational stability of the surgical guiding tool is obtained by the fact that the contact surfaces of the different lateral contact elements have an arrangement around the socket and socket labrum, wherein for every pair of adjacent contact points not belonging to the same contact surface, the angle between the line drawn between one contact point and the center of the circle best fitting the socket rim and a second line drawn between the adjacent contact point and the center is never greater than 180°. Again, a similar embodiment can be envisaged for a piriform or elliptical socket (glenoid cavity).

Alternative or specific combinations of the above are also envisaged. In certain embodiments, as indicated above, the surgical guiding tools as described herein may comprise only one lateral contact element, which comprises several patient-specific contact surfaces. In other embodiments, the surgical guiding tools as described herein may comprise at least two lateral contact elements, each comprising one or more patient-specific contact surfaces as described herein above. In certain embodiments, the surgical guiding tools as described herein may comprise three or more lateral contact elements, each comprising one or more patient-specific contact surfaces as described herein above. It will be understood to the skilled person that, in the guiding tools as described herein the different lateral contact elements need not make contact with the anatomy in the same way and need not contact the anatomy over their entire surface.

In particular embodiments, it can be envisaged that at least one lateral contact element is positioned on the guiding tool such that, when placed on the socket rim, its patient-specific surface corresponds to the surface of the corresponding socket in the location of a conspicuous anatomical feature around the socket labrum. For the glenoid cavity, this can be for example the coracoid process (processus coracoideus); this is a small hook-like structure on the lateral edge of the superior anterior portion of the scapula. For the acetabulum, this can be for example the posterior notch of the transverse ligament, hereinafter also referred to as "posterior notch". The provision of a contact element which fits into or against such a feature such as the posterior notch or the coracoid process further ensures a stable positioning of the surgical guiding tool onto the socket. Thus, in particular embodiments, the surgical guiding tools as described herein are designed such that they comprise at least one lateral contact element which interacts with an anatomical feature on the anatomy surrounding the socket labrum. In particular embodiments, the lateral contact element is to be positioned within the posterior notch or the coracoid process.

In particular embodiments, the surgical guiding tools as described herein further comprise a positioning element. The positioning element is a part of the guiding tool which is used for use with an alignment tool. In particular embodiments, the positioning element is designed to allow placing an alignment element onto or into the socket or the bone surrounding the socket in a pre-operationally planned position. The bone surrounding the socket suitable for placing the alignment element may be, for example, the bone in the periglenoidal region (e.g. infraglenoidal tuberculum, supraglenoidal tuberculum and collum scapulae, etc.) or periacetabular region (e.g. the limbus acetabuli, sulcus supraacetabularis, superior ramus, etc.). Therefore, the positioning element may be provided with at least one hole or slit which either guides or allows the insertion of an alignment element, such as a pin. In particular embodiments, the positioning element is designed for use with alignment means such as a laser. In these embodiments, the positioning element can be either a physical shape or an electronic device such as a sensor.

In particular embodiments, the central contact element, the lateral contact element(s) and the positioning element in the surgical guiding tool, allow for the correct positioning of an alignment element.

The desired position of the alignment element for guiding the placement of an implant is determined by pre-operative planning. Moreover, using preoperative planning, optimal contact points for the lateral contact element(s) of the surgical guiding tool as described herein can be determined. Indeed, while the number and shape of the contact elements may vary, the contact points or surfaces provided thereon determine the stability of the guiding tool. The optimal position of the contact points/surfaces ensures positional stability of the surgical guiding tool onto the socket.

In particular embodiments, the positioning element is located on the central contact element. More particularly, the central contact element comprises a hole which serves as a positioning element.

In particular embodiments, the surgical guiding tools as described herein allow correct positioning of an alignment element by way of a positioning element. The positioning element may thus comprises an opening or hole which allows the insertion of an alignment element which is guided by the positioning element into the socket or into the bone surrounding the socket. The alignment element may be a wire, pin, screw or drill, particularly a metal wire, pin, screw or drill. In particular embodiments, the alignment element is a wire or a pin, particularly a Kirschner wire (K-wire) or a Hoffmann pin.

In order to allow the guiding of the positioning of an implant for a socket of a ball-joint, the alignment element is typically positioned on the socket or on the bone of surrounding the socket in a direction parallel to the installation direction of the implant. The optimal orientation of the opening of the positioning element can be obtained by determining the orientation of the positioning element according to pre-operational planning. Thus, in certain embodiments, the direction and/ or the position of at least one hole of the surgical guiding tools as described herein which allows the insertion of an alignment element is in accordance with pre-operational planning. This allows the use of standard alignment elements such as K-wires. The positioning and/or orientation of the hole can be obtained via a certain location and/or orientation of the positioning element relative to the rest of the surgical guiding tool, via a certain location and/or position of the hole in the positioning element, or via a combination of the two. Additionally or alternatively, the shape of the alignment element itself can be provided such that, when inserted into the positioning element, it ensures the correct orientation to guide the implant.

As described herein above, the central contact element and the lateral contact element(s) may contact different areas of the anatomy of the socket. In particular embodiments, it can be of interest to avoid contact with the socket labrum. To this end, it can be envisaged that the contact elements as well as any connections between the lateral and central contact elements "bridge" the labrum. In further embodiments, the contact elements may extend over at least part of the labrum and an adjoining section of the interior surface of the socket and/or exterior surface of the bone comprising the socket. In particular embodiments, the contact element(s) contact(s) only the exterior surface of the bone comprising the socket.

In particular embodiments, the central and lateral contact elements are interconnected. More particularly, the connecting structures between these elements are selected such as to ensure stable connection while reducing visual impairment during surgery. Thus in particular embodiments, each lateral contact element is discretely connected to the central contact element. Where the lateral contact elements extend over a larger section of the rim (i.e. more than 10°) two or more discrete connections with the central contact element may be provided. In certain embodiments, the surgical guiding tools as described herein comprise a connecting structure, wherein the one or more lateral and central contact elements extend from the connecting structure. In further embodiments, two or more contact elements extend from the connecting structure. In certain embodiments, the connecting structure is a central element, particularly a central axis. In particular embodiments, the contact element(s) and/or the positioning element(s) are separate units which are connectable to the connecting structure, central element or axis. In alternative embodiments, the surgical guiding tools as described herein are manufactured as a single piece. In particular embodiments, the connecting structure incorporates the positioning element and/or the central contact element.

The surgical guiding tools as described herein may further contain additional features, such as guiding features or handling features. Guiding features may be used to guide a surgical tool, such as a drill or a blade. Handling features are used for the manual handling and positioning of the device and can include features such as knobs (e.g. for holding the tool), dents (e.g. for applying pressure to the tool when pushing it into position), hooks or other attachment features (for attachment of other tools) etc. The presence of such dedicated features is not critical.

Further provided herein are methods for the manufacture or generation of the surgical guiding tools described herein. The surgical guiding tools described herein comprise contact elements, the position of which is adjusted to correspond to the specific anatomy of the patient.

In particular embodiments as described above, the surgical guiding tools as described herein comprise patient-specific contact points and/or surfaces. The generation of patient-specific surgical guiding tools is done based on pre-operative images of the anatomy surrounding the socket of the joint under consideration, and planning of the surgery. More particularly, the generation of patient-specific surgical guiding tools is done based on preoperative images of the socket, and planning of the surgery. Accordingly, methods for producing the surgical guiding tools as described herein typically comprise the steps of: a) obtaining volume information of the socket of a ball-and-socket joint from a patient; b) obtaining the installation direction of a socket implant for the patient; c) identifying and selecting parts of the bone surrounding the socket which are suitable for lateral contact elements; d) designing and generating a surgical guiding tool based on the information obtained in steps a), b) and c).

More particularly, the surgical guiding tool designed in step (d) comprises a central contact element which fits onto an area within the socket of the ball-and- socket joint; one or more lateral contact elements which fit onto the rim of the socket and/or the bone surrounding the socket and/or the ligament around the socket; and a positioning element provided with a feature, such as an opening, which allows the interaction with an alignment tool.

Generating the guiding instrument may include designing a model of a guiding instrument or an image thereof. The design of the guiding instrument may further be provided on an information carrier or can be sent to a manufacturing facility for the manufacturing of the guiding instrument or parts thereof. In particular embodiments, the methods described herein include manufacturing the guiding instrument or parts thereof.

The step of obtaining volume information of the socket typically comprises obtaining digital patient-specific image information which can be done by any suitable means known in the art, such as for example a computer tomography (CT) scanner, a magnetic resonance imaging (MRI) scanner, an ultrasound scanner, or a combination of Roentgenograms. A summary of medical imaging has been described in "Fundamentals of Medical imaging", by P. Suetens, Cambridge University Press, 2002. In a particular embodiment, Additive Manufacturing (AM) techniques are used for manufacturing the surgical guiding tools as described herein, or parts thereof. AM techniques are particularly useful to manufacture patient-specific contact surfaces, or to produce the surgical guiding tools in one piece. As an example, the manufacturing of medical-image-based patient-specific surgical instruments via AM is described in U.S. Pat. No. 5,768,134 (Swaelens et al).

AM can be defined as a group of techniques used to fabricate a tangible model of an object typically using three-dimensional (3-D) computer aided design (CAD) data of the object. Currently, a multitude of Additive Manufacturing techniques is available, including stereolithography, Selective Laser Sintering, Fused Deposition Modeling, foil-based techniques, etc. Selective laser sintering uses a high power laser or another focused heat source to sinter or weld small particles of plastic, metal, or ceramic powders into a mass representing the 3-dimensional object to be formed. Fused deposition modeling and related techniques make use of a temporary transition from a solid material to a liquid state, usually due to heating. The material is driven through an extrusion nozzle in a controlled way and deposited in the required place as described among others in U.S. Pat. No. 5,141,680. Foil-based techniques fix coats to one another by means of gluing or photo polymerization or other techniques and cut the object from these coats or polymerize the object.

Typically AM techniques start from a digital representation of the 3-D object to be formed. Generally, the digital representation is sliced into a series of cross-sectional layers which can be overlaid to form the object as a whole. The AM apparatus uses this data for building the object on a layer-by-layer basis. The cross-sectional data representing the layer data of the 3-D object may be generated using a computer system and computer aided design and manufacturing (CAD/CAM) software.

The surgical guiding tools as described herein may be manufactured in different materials. Typically, only materials that are biocompatible (e.g. USP class VI compatible) with the animal or human body are taken into account. Preferably the surgical guiding tool is formed from a heat-tolerable material allowing it to tolerate high-temperature sterilization. In the case selective laser sintering is used as an AM technique, the surgical template may be fabricated from a polyamide such as PA 2200 as supplied by EOS, Munich, Germany or any other material known by those skilled in the art may also be used.

Also provided herein are methods for using surgical guiding tools such as those characterized by the features described herein. More particularly, methods are provided for placing an alignment element into a socket or into the bone surrounding a socket. The methods comprise the steps of:

(i) positioning a surgical guiding tool as described herein onto the socket;

(ii) using the feature provided by the positioning element of the guiding tool provide an alignment tool into or on the bone of or around the socket;

(iii) removing the guiding tool from the socket.

In particular embodiments, the alignment tool is an alignment element, such as a pin. In further embodiments, the alignment element is maintained in the bone during removal of the guiding tool from the socket.

Also provided herein are methods for guiding an implant in a socket of a ball joint such as an acetabulum or glenoid cavity. These methods may comprise steps (i), (ii) and (iii) as described herein above and further comprise the step of:

(iv) Using the alignment element positioned in the bone to obtain the correct implant direction; in particular embodiments this is the direction according to the preoperational planning.

It is noted that the alignment element envisaged in the present context may be used as a visual alignment element or a physical alignment element. In particular embodiments, the alignment element is a pin or wire and is used as a physical alignment element to guide an implant or implant guide onto the bone in the correct position. Typically the implant or implant guide will comprise a hole or slit which is positioned such that, when the hole or slit of the implant or implant guide is mated with the alignment feature, it will guide the implant and/or implant guide directly in the desired position on the socket of the ball joint.

EXAMPLE

Figure 1B:
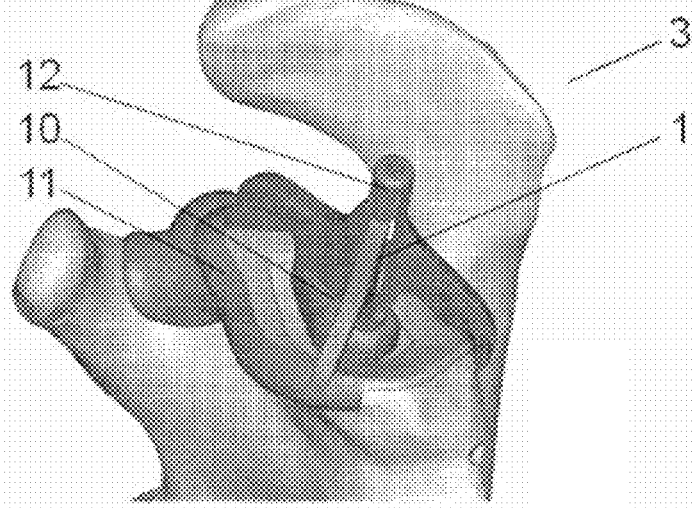
FIG. 1B is a perspective view of a surgical guiding tool (1) according to a particular embodiment, positioned on a glenoid cavity (2) of a ball-and-socket joint (3).

FIGS. 1A and 1B show a perspective view of a ball-and-socket joint (3) and the glenoid cavity (2) of a ball-and-socket joint (3). A surgical guiding tool (1) as described herein is positioned onto a glenoid cavity (2) of a ball-and-socket joint (3).

The surgical guiding tool typically comprises as central contact element (10) which fits onto the inner surface of the socket of the ball-and-socket joint; one or more lateral contact elements (11) which fit onto the bone surrounding the socket; and a positioning element (12) provided with an opening which allows the insertion of the alignment element.

FIG. 2A shows a side view of a surgical guiding tool (1) according to a particular embodiment as described herein, positioned on a glenoid cavity (2) of the ball-and-socket joint (3). Also shown is an example of an alignment element (13) which can be inserted into the positioning element (12). FIG. 2B shows the top view of the surgical guiding tool (1) according to a particular embodiment, positioned on a glenoid cavity (2) of a ball-and-socket joint (3). FIGS. 3A-3C show the surgical guiding tool (1) according to a particular embodiment as described herein, more particularly as seen from different angles.

Figure 4A:
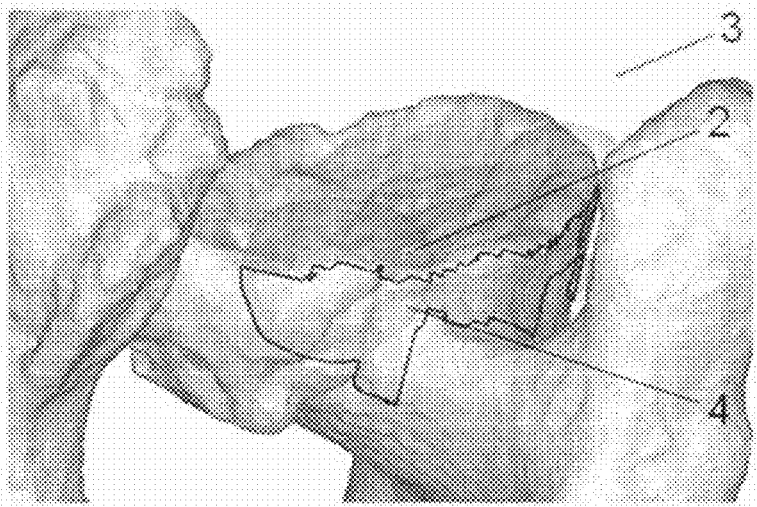
FIG. 4A is an illustration of a glenoid for which an outer contour surface (4) has been determined.
Figure 4B:
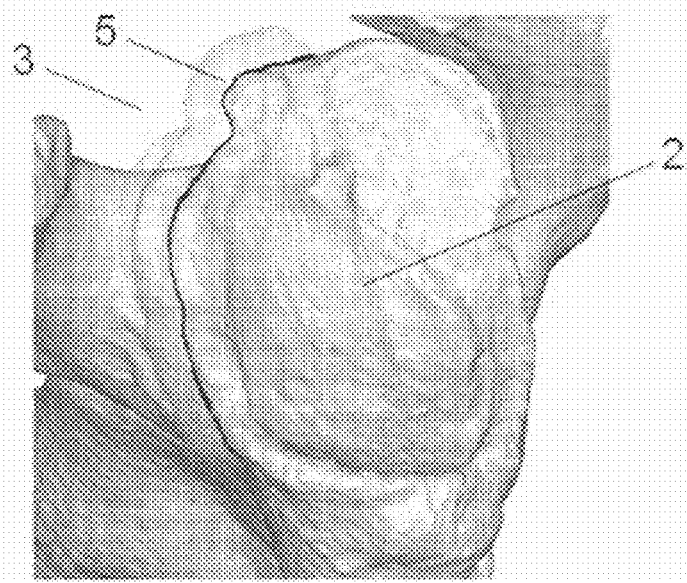
FIG. 4B is an illustration of a glenoid for which a contour line (5) has been determined.

FIGS. 4A and 4B illustrate a glenoid (3) for which a contour line (5) and outer contour surface (4) has been determined. This anatomical information is used for generating a patient-specific surgical guiding tool according to particular embodiments as described herein. In these embodiments, the one or more lateral contact elements extend longitudinally over a section of rim of the glenoid cavity and extend transversally over the rim of the glenoid cavity (i.e. from the inner surface to the outer surface of the bone).

FIGS. 5A-5C illustrate the design of a surgical guiding tool (1) according to an embodiment envisaged herein. In this embodiment, the tool (1) comprises only one lateral contact element (11) which extends longitudinally over a section of the rim of the socket and extends transversally over the rim of the glenoid cavity. The lateral contact element (11) is connected to the central contact element (12) in two points.

What is claimed is:

1. A patient-specific surgical guiding tool for positioning an alignment element, the patient-specific guiding tool comprising:
    a central contact element configured to fit onto an area of a socket of a ball-and-socket joint, wherein the ball-and-socket is an acetabulum;
    one or more lateral contact elements configured to fit onto at least one of the following: a rim of the socket, a bone surrounding the socket, and a ligament around the socket, wherein at least one of the one or more lateral contact elements is configured to fit onto a posterior notch of a transverse ligament of the ball-and-socket joint; and
    a positioning element comprising a feature configured to receive the alignment element,
    wherein at least one of the one or more lateral contact elements comprises a contact surface corresponding to at least part of an outer contour of the socket and the central contact element comprises a contact surface corresponding to at least part of an inner surface of the socket.

2. The patient-specific surgical guiding tool of claim 1, wherein the rim of the socket defines at least one of a substantially circular shape or a roughly elliptical shape having a center defined by a circle best fitting the substantially circular shape or by an ellipse best fitting the roughly elliptical shape, wherein the one or more lateral contact elements comprises at least two lateral contact elements configured to contact the socket in at least three contact points, wherein, for each contact point of the at least three contact points, an angle between a first line connecting the contact point and the center and a second line connecting an adjacent contact point and the center is not greater than 180°, wherein the adjacent contact point is one of the at least three contact points.

3. The patient-specific surgical guiding tool of claim 1, further comprising a connecting structure, the one or more lateral contact elements extending from the connecting structure.

4. The patient-specific surgical guiding tool of claim 3, wherein the connecting structure corresponds with the positioning element.

5. The patient-specific surgical guiding tool of claim 1, wherein at least one of the one or more lateral contact elements corresponds with an anatomical feature around the socket.

6. The patient-specific surgical guiding tool of claim 1, wherein the alignment element comprises at least one of the following: a pin, a wire, a screw and a drill.

7. The patient-specific surgical guiding tool of claim 1, wherein the positioning element corresponds to at least one of the central contact element and the one or more lateral contact elements.

8. The patient-specific surgical guiding tool of claim 1, wherein the socket is an acetabulum cavity.

9. A method of positioning an alignment tool on bone, the method comprising:
    positioning a surgical guiding tool onto a socket of a ball-and-socket joint, wherein the ball-and-socket joint is an acetabulum, and wherein the surgical guiding tool comprises:
        a central contact element configured to fit onto an area of the socket;
        one or more lateral contact elements configured to fit onto at least one of the following: a rim of the socket, a bone surrounding the socket, and a ligament around the socket, wherein at least one of the one or more lateral contact elements is configured to fit onto a posterior notch of a transverse ligament of the ball-and-socket joint; and
        a positioning element comprising a feature configured to receive the alignment tool;
    positioning the alignment tool on or into the bone of or around the socket by inserting it through an aperture defined by the positioning element; and
    removing the surgical guiding tool from the socket.

10. The method of claim 9, wherein the alignment tool comprises a pin and step alignment element, and wherein removing the surgical guiding tool further comprises removing the surgical guiding tool from the socket along a direction of a longitudinal axis of the alignment element without removing the alignment element from the bone.

\* \* \* \* \*